United States Patent [19]
Falconer

[11] Patent Number: 5,938,176
[45] Date of Patent: Aug. 17, 1999

[54] TAP OR VALVE

[75] Inventor: Malcolm Ian Falconer, London, United Kingdom

[73] Assignee: Bristol-Myers Squibb Company, New York, N.Y.

[21] Appl. No.: 08/641,594

[22] Filed: May 1, 1996

[30] Foreign Application Priority Data

Nov. 14, 1995 [GB] United Kingdom .................... 9523305

[51] Int. Cl.$^6$ .................................................. A61M 27/00
[52] U.S. Cl. ............................................ 251/342; 251/341
[58] Field of Search ...................................... 251/342, 341

[56] References Cited

U.S. PATENT DOCUMENTS

| | | | |
|---|---|---|---|
| 3,827,439 | 8/1974 | Schulte et al. | 251/342 |
| 4,106,675 | 8/1978 | Taylor | 251/342 |

FOREIGN PATENT DOCUMENTS

| | | | |
|---|---|---|---|
| 6460 | 3/1994 | United Kingdom | 251/342 |

*Primary Examiner*—A Michael Chambers
*Attorney, Agent, or Firm*—Stuart E. Krieger

[57] ABSTRACT

An aim of the invention is to provide a simple and effective one-piece tap which can be readily and economically manufactured. A tap for a liquid container is made from natural or synthetic rubber or a resilient plastics material. It has a base portion 10 having an orifice 12 which serves as a liquid inlet therein, the base portion embodying a liquid exit means 14. It also has a resilient deformable closure portion 20, the closure portion being constructed to make a resilient snap-on connection with the periphery of the base portion, the closure portion being manipulatable and having a centrally located plug 22 extending towards the base portion. This plug can obturate orifice 12 thereby closing the liquid inlet. The closure portion 20 also has a projecting portion 23 extending generally perpendicularly away from the base portion, the projecting portion being constructed so that it can be pushed towards the base portion in order to remove the plug from the orifice and so permit liquid to pass to the liquid exit means 14.

9 Claims, 3 Drawing Sheets

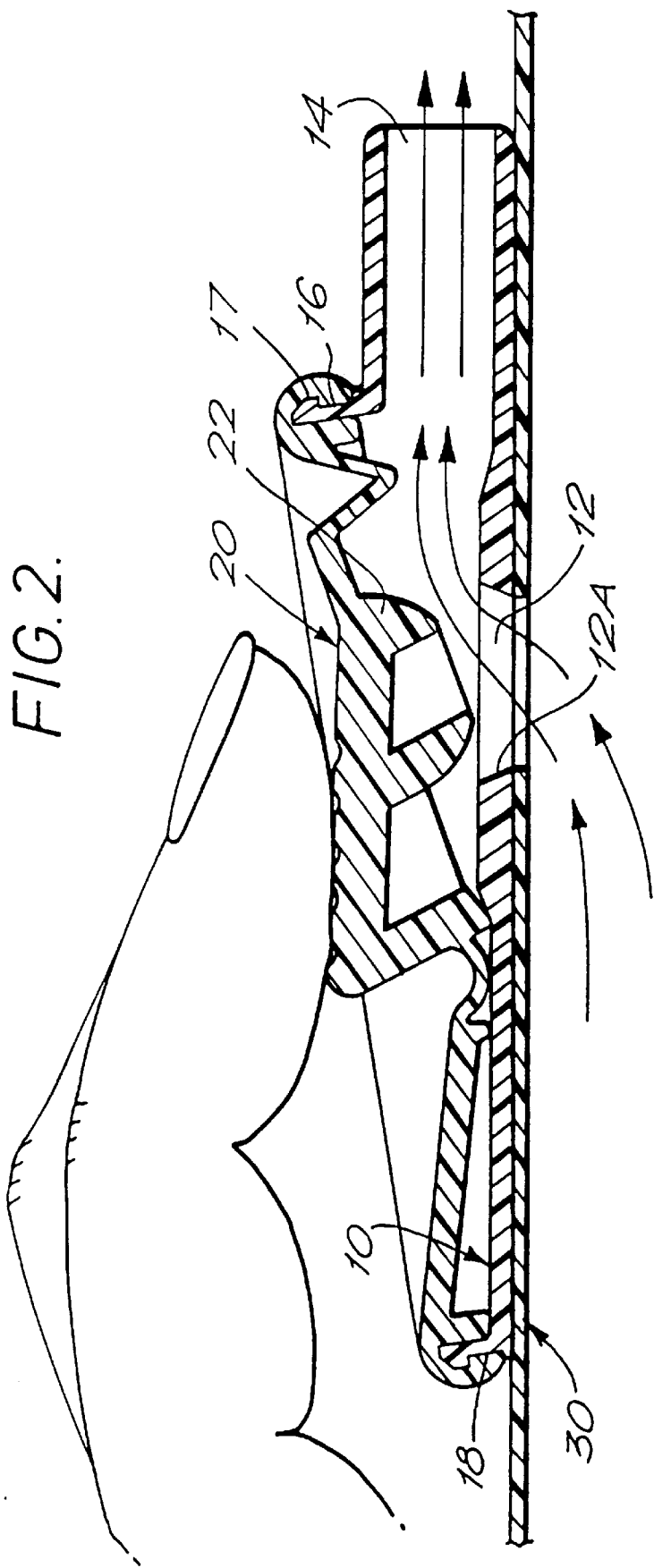

TAP OR VALVE

BACKGROUND OF THE INVENTION

This invention relates to a tap or valve and particularly although not exclusively to a tap for a urostomy pouch.

Various designs of taps or dispensing spigots have been proposed. See for examaple Fattori et al U.S. Pat. Nos. 3,400,866 and 4,787,538, Welsh U.S. Pat. No. 3,972,452, European Patent Application No. 95861A and Scholle U.S. Pat. No. 4,211,348. These designs, in the Applicants' opinion, fall short in that they are lacking in simplicity. Most are completely unsuitable for employment in a urostomy pouch.

It is an aim of the invention to provide a simple and effective easily-assembled tap which can be readily and economically manufactured.

According to the invention there is provided a tap for a liquid container, made from natural or synthetic rubber or a resilient plastics material, which comprises a base portion having an orifice which serves as a liquid inlet therein, the base portion embodying a liquid exit means, and a resilient deformable closure portion, the closure portion being constructed to make a resilient snap-on connection with the periphery of the base portion, the closure portion being manipulatable and having a centrally located plug extending towards the base portion which can obturate said orifice thereby closing the liquid inlet, the closure portion also having a projecting portion extending generally perpendicularly away from the base portion, the projecting portion being constructed so that it can be pushed towards the base portion in order to remove the plug from the orifice and so permit liquid to pass to the liquid exit means.

In a preferred embodiment of the invention, the closure portion is a wall which is generally oval in shape as seen in front elevation and has an external thickened sloping portion upon which the said plug is internally mounted. The sloping portion is located generally centrally of the closure portion. In the embodiment of the invention which consists of a urostomy pouch, the base portion including the liquid exit means thereof is constructed for attachment, e.g. by heat or R.F. welding, to one wall of the pouch, the pouch having an aperture in one of its walls, the aperture being in registry with the liquid inlet orifice.

In an advantageous embodiment of the invention, a night drainage adapter may be used with, and temporarily incorporated in, the tap described and illustrated herein. This adapter device comprises a tube extension of a particular shape which when inserted into the liquid exit means, holds the closure portion away from the liquid entry hole in the base portion. This permits intermittent night drainage to occur, with no manipulation to open the tap being necessary.

BRIEF DESCRIPTION OF THE DRAWINGS

The invention will be better understood from the following description of an illustrative embodiment, in which like parts are represented by like reference numerals, and in which:

OBJECTS AND SUMMARY OF THE INVENTION

Figure 1:
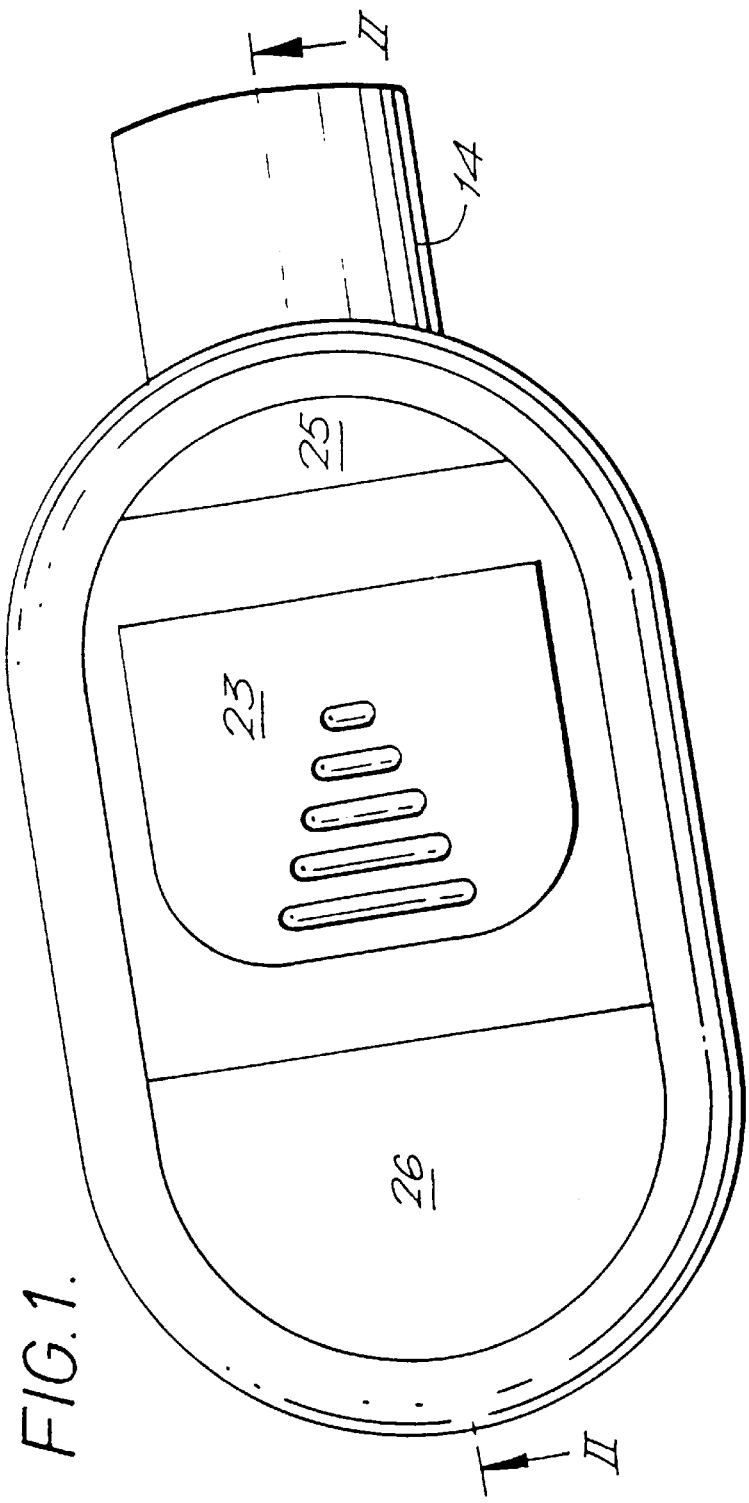
Figure 3:
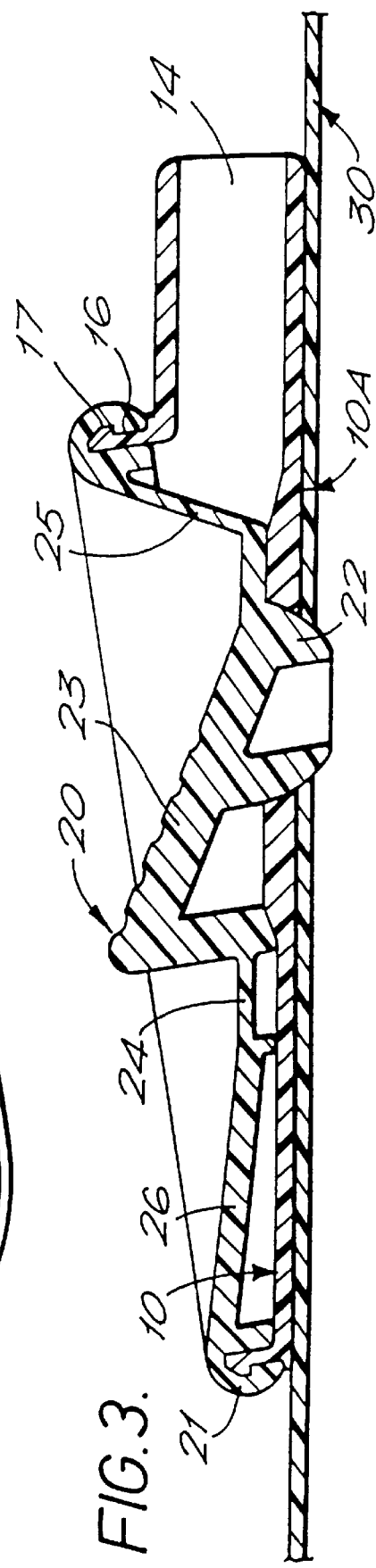
Figure 4:
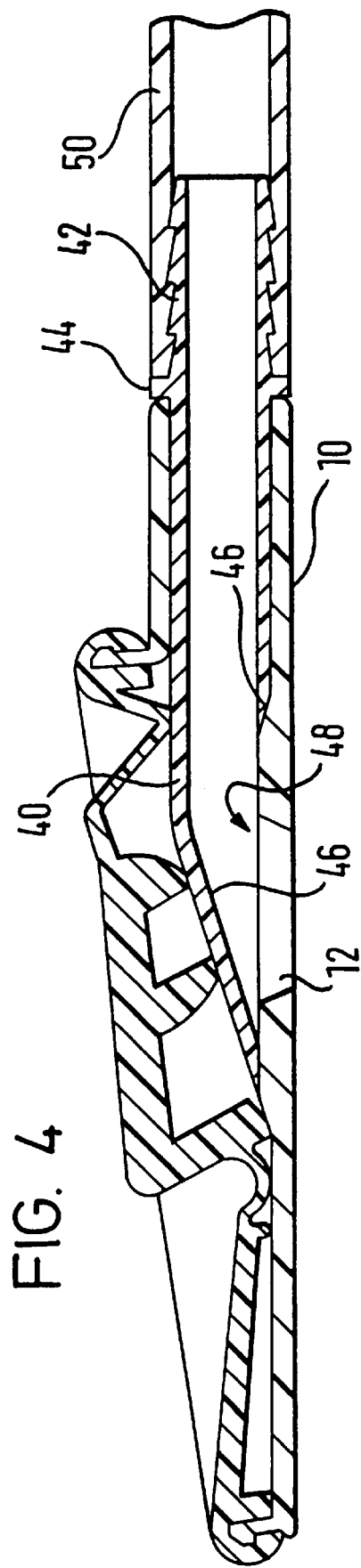
Figure 5:
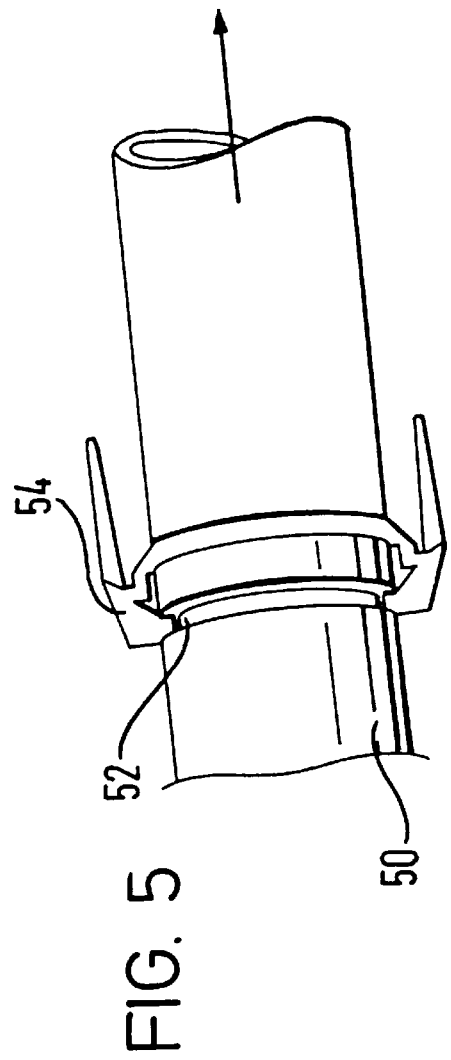

FIG. 1 is a front view of one example of tap according to the invention;

FIG. 2 is a cross-section on the plane II—II in FIG. 1 showing the tap in its open condition and diagrammatically illustrating part of a wall of a urostomy pouch;

FIG. 3 is a view identical to FIG. 2 but showing the tap in its normally closed condition;

FIG. 4 is a cross-sectional view of a tap having a night drainage adapter in place; and FIG. 5 illustrates an optional refinement in the form of a peripheral groove on the drain tube, which allows attachment of a known type of tube connector (see UK Patent 2,092,690; EP 57057B; and UK Patent Application No. 9514011.7).

DETAILED DESCRIPTION OF THE DRAWINGS

Referring to FIGS. 1–3, the illustrated tap comprises a base portion 10 and a closure portion 20. The wall of a urostomy pouch which is the currently preferred example of product in which the tap may be employed, is shown at 30 in FIGS. 2 and 3.

The base portion 10 comprises a central orifice 12 and embodies a liquid exit means 14. The base portion has a peripheral wall 16, and carried by this wall is an outwardly extending rim 17 provided to enable snap-on engagement between itself and a connection means 21 on the periphery of the closure portion 20. The base portion 10 has a flat surface 10A which may be plastics welded or adhesively secured or fastened in any other convenient way to the wall 30 of the liquid container.

The peripheral snap-on connection means 21 of the closure portion is designed to co-operate with the peripheral wall 16 of the base portion. The closure portion is made of a resilient deformable material, preferably a thermoplastics elastomer. The closure portion has a centrally located plug 22, which extends towards the base portion 10 and is shaped to make a complementary mating engagement with the wall 12A of the orifice 12. The closure portion has a peripheral slot 18, in which is received the wall 16.

The left-hand end as seen in FIG. 2 or FIG. 3 of the base and closure portions will be uppermost in use of the tap, with the liquid exit means 14 being lowermost.

The closure portion 20 is a plastics moulding, and has a thickened portion 23 which in the closed position of the tap is at an angle to the vertical and in the tap's open position occupies an approximately vertical position. This may be achieved by manipulating the closure portion 20 with a finger as illustrated in FIG. 2. This manipulation is faciliated by the fact that the thickness of the closure portion is substantially reduced at the zones 24 and 25 and is reduced but to a lesser extent at the zone 26. The zones 24 and 25 readily deform to enable the closure portion to take up its open position as illustrated in FIG. 2.

One desirable advantage of this design of tap is that its overall thickness is small. Hence, a pouch having this design of tap is unobtrusive when worn. Another advantage is that the closure portion 20 immediately reverts to the closed position as seen in FIG. 3 when the finger pressure is removed from the portion 23 thereof. The complementary shaping of the plug 22 and the wall 12A, and the interfit between the parts 16, 17, 18, assist in achieving a durable and leakproof fit. The tap as illustrated in FIGS. 1–3 has no detachable parts which might become misplaced or lost.

A night drainage adapter 40 is illustrated in FIG. 4 in position within the tap. The adapter 40 comprises a tapered tube having a ribbed end 42, a flange 44, a taper 46 at its upper end in use, and a hole 48 of a size slightly greater than the holle 12 in the base portion 10. The ribbed end 42 facilitates connection to a drain tube 50. As will be seen in FIG. 4, the adapter 40 when inserted upwardly into the tap, forces the closure portion away from the base portion 10. The resilience of the closure portion holds the adaptor 40 into close engagement with the surface of the base portion. Liquid entering via hole 12 is then guided by adapter 40 directly to the train tube 50.

Referring now to FIG. 5, at the lower end of the train tube 50 a peripheral groove 52 is provided, to receive hook members 54 of a known connector, provided to convey liquid, e.g. to a night drainage bag or reservoir.

What is claimed is:

1. A tap for a liquid container, made from natural or synthetic rubber or a resilient plastics material, comprising:

a base portion having an orifice which serves as a liquid inlet therein, a closure portion connected to said base portion so as to define a chamber, said chamber having a liquid outlet, said closure portion having a non-deformable zone and a deformable hinged zone, said non-deformable zone being pushable and having a plug extending therefrom into said chamber which in the absence of pushing said non-deformable zone is biased so as to obturate said orifice and close said liquid inlet, said non-deformable zone being pushable so as to deform at said deformable hinged zone and remove said plug from said inlet orifice and permit the liquid to pass through said inlet orifice, said chamber and said liquid outlet.

2. The tap according to claim 1 wherein said non-deformable zone is thicker than said hinged zone.

3. The tap according to claim 2 wherein said non-deformable zone has a sloping surface upon which said plug is mounted.

4. The tap according to claim 3 wherein said sloping surface is located substantially centrally of said closure portion.

5. The tap according to claim 1 further comprising a urostomy pouch liquid container having a front and rear wall with at least one of said walls having a hole, said liquid outlet being attached a wall of said pouch with said orifice in registry with said hole in said pouch wall.

6. The tap according to claim 1 wherein said liquid outlet is in fluid communication with a night drainage adapter.

7. The tap according to claim 6 wherein said night drainage adapter includes a tube having an end portion insertable into said liquid outlet so as to prevent obturation by said plug of said liquid inlet.

8. The tap according to claim 7 wherein said end portion of said the tube is tapered.

9. The tap according to claim 7 wherein said tube is shaped to force, upon insertion of said tube into said liquid outlet, said closure portion away from said base portion and said plug from said inlet orifice.

* * * * *